US007049448B2

(12) United States Patent
Reguri et al.

(10) Patent No.: US 7,049,448 B2
(45) Date of Patent: May 23, 2006

(54) PROCESS FOR THE PREPARATION OF MONOKETALS OF 1,4-CYCLOHEXANEDIONE INCLUDING 1, 4-CYCLOHEXANEDIONE MONO-2,2-DIMETHYL TRIMETHYLENE KETAL

(75) Inventors: Buchi Reddy Reguri, Hyderabad (IN); Rajasekhar Kadaboina, Hyderabad (IN); Srinivas Reddy Gade, Hyderabad (IN); Babu Ireni, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 10/662,980

(22) Filed: Sep. 15, 2003

(65) Prior Publication Data

US 2004/0230063 A1 Nov. 18, 2004

(30) Foreign Application Priority Data

Sep. 13, 2002 (IN) ......................... 681/MAS/2002

(51) Int. Cl.
*C07D 319/16* (2006.01)
*C07D 317/72* (2006.01)
*C07D 209/88* (2006.01)

(52) U.S. Cl. ....................... 549/341; 549/333; 548/441

(58) Field of Classification Search ................ 549/333, 549/341; 548/441
See application file for complete search history.

(56) References Cited

FOREIGN PATENT DOCUMENTS

FR 2827602 * 1/2003

OTHER PUBLICATIONS

Courtot, Bull Soc. Chim. Fr., p. 1493-1494 (1962).*

* cited by examiner

*Primary Examiner*—Bernard Dentz
(74) *Attorney, Agent, or Firm*—Robert A. Franks; Edward D. Pergament; Milagros A. Cepeda

(57) ABSTRACT

There is provided a process for preparation of a monoketal compound of the structure that includes reacting 1,4-cyclohexanedione of the structure with a diol of the structure in a halogenated organic solvent in the presence of an acid catalyst, wherein X is a substituted or unsubstituted ethylene or propylene. Various embodiments and variants are provided.

27 Claims, No Drawings

PROCESS FOR THE PREPARATION OF MONOKETALS OF 1,4-CYCLOHEXANEDIONE INCLUDING 1,4-CYCLOHEXANEDIONE MONO-2,2-DIMETHYL TRIMETHYLENE KETAL

CROSS REFERENCE TO RELATED APPLICATIONS

This application claims benefit of the filing date of Indian Patent Application No. 681/MAS/2002, filed Sep. 13, 2002, the content of which is expressly incorporated herein by reference in its entirety.

FIELD OF THE INVENTION

The present invention relates to an improved process for the preparation of monoketals of 1,4-cyclohexanedione, including 1,4-cyclohexanedione mono-2,2-dimethyl trimethylene ketal, an intermediate for a number active pharmaceutical ingredients (API) including frovatriptan.

BACKGROUND OF THE INVENTION 1,4-cyclohexanedione mono-2,2-dimethyl trimethylene ketal is an intermediate in the synthesis of (+)-R-2,3,4,9-tetrahydro-3-(methylamino)-1H-carbazole-6-carboxamide butanedioate, frovatriptan, which is a serotonin (5-HT) receptor agonist and is known as anti-migraine drug. A few synthetic methods for 1,4-cyclohexanedione mono-2,2-dimethyl trimethylene ketal are known in the art.

*Journal of Synthetic Communications* 9(2), 123–127 (1979) disclosed a process for the preparation of 1,4-cyclohexane dione mono-2,2-dimethyl trimethylene ketal using Birch reduction of 4-methoxy phenol with lithium and ammonia in presence of ethanol to yield 4-methoxy-3-cyclohexene-1-ol, which is further reacted with neopentyl glycol using PTSA in benzene medium gave 2,3-dimethyl-1,3-dipropylene ketal of 4-hydroxycyclohexanone. Oxidation of the resulting ketal with pyridinium chlorochromate yields the 1,4-cyclohexanedione mono-2,2-dimethyl trimethylene ketal. *Journal of Synthetic Communications,* 14 (1), 39–44 (1984) disclosed a process for preparation of 1,4-cyclohexanedione mono-2,2-dimethyl trimethylene ketal that includes continuous extraction of an aqueous solution of 1,4-cyclohexane dione containing 2,2-dimethyl-1,3-propane diol in molar excess and sulfuric acid as the catalyst to afford the 1,4 cyclohexanedione mono-2,2-dimethyl trimethylene ketal. Nevertheless, there is still a need for an improved process suitable for a commercial scale production of 1,4-cyclohexanedione mono-2,2-dimethyl trimethylene ketal

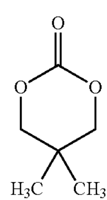

and structurally related compound.

SUMMARY OF THE INVENTION

In accordance with one aspect, the invention provides an improved process for preparation of monoketals of 1,4-cyclohexanediones of the structure

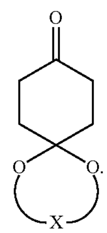

In one embodiment, the process includes reacting 1,4-cyclohexanedione of the structure

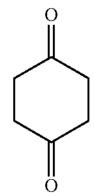

with a diol of the structure

OH OH X in a halogenated organic solvent in the presence of an acid catalyst, where X is substituted or unsubstituted ethylene or propylene. In another embodiment, the invention provides for preparing 1,4-cyclohexanedione mono-2,2-dimethyl trimethylene ketal that includes reacting 1,4-cyclohexanedione of the structure with a diol of the structure

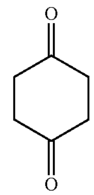

with a diol of the structure

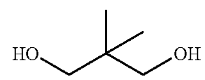

in a halogenated organic solvent in the presence of an acid catalyst. In another embodiment, the process includes a. reacting 1,4-cyclohexanedion and neopentyl glycol in a halogenated solvent in the presence of an acid catalyst;

b. removing the halogenated solvent to provide a crude residue;
c. providing said crude residue in an aliphatic or alicyclic hydrocarbon solvent to form a mixture; and
d. filtering the mixture.

DETAILED DESCRIPTION OF THE PREFERRED EMBODIMENTS

The preparation of a monoketal of 1,4-cyclohexanedione may include a condensation reaction of 1,4-cyclohexanedione with a diol having the structure

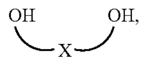

where X is a substituted or unsubstituted ethylene or propylene. Non-limiting examples of suitable diols include ethylene glycol, propylene glycol, neopentyl glycol or 1,3-propanediol. Particularly, when the diol is neopentyl glycol, the product of the condensation is 1,4-cyclohexanedione mono-2,2-dimethyl trimethylene ketal. In a particular embodiment, the invention therefore provides a process for preparation of 1,4-cyclohexanedione mono-2,2-dimethyl trimethylene ketal via a reaction between neopentyl glycol and 1,4-cyclohexanedione.

The reaction is carried out in a halogenated solvent in the presence of acid catalyst. For example, 1,4-cyclohexanedione and the diol may be dissolved together in the halogenated solvent before the acid catalyst is added thereto. Alternatively, the solution of each reactant may be prepared separately and later combined in a desired order. The halogenated solvent is preferably $C_1$–$C_3$ haloalkane. Non-limiting examples of suitable $C_1$–$C_3$ haloalkanes include chloroform, dichloromethane, dichloroethane, carbon tetrachloride, and mixtures thereof. The acid catalyst of the process can be any conventional acids, which is preferably adoptable for a commercial scale of the reaction and can be used in the halogenated solvents of the process. Non-limiting examples of suitable acid catalysts are hydrochloric acid, p-toluenesulfonic acid, sulfuric acid, fumaric acid, phthalic acid, oxalic acid and mixtures thereof. The acid catalyst may be supplied to the condensation reaction by itself or in a solvent.

The condensation reaction may be carried out at an ambient temperature or elevated temperature. The preferred temperature range for the condensation reaction is between about 25° C. and about 50° C., more preferably between about 25° C. and about 30° C.

The molar ratio between 1,4-cyclohexanedion and the diol to be used in the condensation reaction preferably ranges from about 1:1 to about 1:4; more preferably the range is from about 1:1 to about 1:2; and yet more preferably the molar ratio is about 1:1. However, the molar ratio may be altered, if desired. For example, the smaller amount of the diol than that of 1,4-cyclohexanedion may be used in the condensation reaction although the reaction yield may be affected thereby. In the condensation reaction of this aspect of the invention, the weight/volume ratio of 1,4 -cyclohexanedion to the halogenated organic solvent preferably ranges from about 1:1 to about 1:20, and more preferable the weight/volume ratio is about 1:8.

It is believed that the process of this aspect of the invention leads to desired intermediates having higher purities than the prior art processes. Also, the process is more suitable for commercial production of the intermediates.

Upon completion of the condensation reaction, the reaction mixture can be subjected to a conventional work-up and isolation procedures. One preferred work-up and isolation process includes washing the reaction mixture with an aqueous base solution; separating the organic layer from resulting biphasic mixture; removing the organic solvent from the separated organic layer to give a crude residue; providing the crude residue in aliphatic or alicyclic hydrocarbon solvent to form a mixture; removing solid impurities from the mixture; and isolating the monoketal product.

The washing of the condensation reaction mixture with an aqueous base can be done preferably at about 0–25° C., more preferably at about 10–20° C. The aqueous base can be water solution of any typical bases as long as it does not affect the stability of the monoketal product. Preferable examples of the base include potassium carbonate, calcium carbonate, ammonium hydroxide and mixtures thereof.

The organic solvent of the organic layer may be removed under reduced pressure but may not have to be removed completely to give essentially dry solid crude residue. A residual amount of the organic solvent left over in the crude residue may be acceptable, especially if it does not affect the followed filtration process using the aliphatic or alicyclic hydrocarbon solvent. Before removal of the organic solvent, the organic layer may be dried over drying agents such as, for example, magnesium sulfate, molecular sieves, etc.

Non-limiting examples of suitable aliphatic or alicyclic hydrocarbon solvents for work-up and isolation process include petroleum, ether, hexane, n-hexane, cyclohexane, n-heptane, cycloheptane or mixtures thereof. The crude residue may be combined with the aliphatic or alicyclic hydrocarbon does not have to be an essentially dried solid. The removal of solid impurities from the reaction mass can be easily obtained by conventional filtration techniques. For example, the filtration can be done using filtration papers or short silica gel columns. Other conventional techniques, which are suitable for such separation of solid impurities from a solution, may also be used. The filtration techniques may be performed at a temperature preferably between about 0° C. and about 25° C., more preferably between about 0° C. and about 5° C. After filtration, the solvent may be optionally distilled off from the filtrate preferably under reduced pressure.

Since the monoketal product of the present invention is mostly likely to be used as a precursor of other compounds such as (+)-(R)-2,3,4,9-tetrahydro-3-(methylamino)-1H-carbazole-6-carboxamide butanedioate, frovatriptan, the isolated monoketal product may be isolated as a solution, solid or wet solid in which the solvent is not completely removed depending upon the characteristics of the use of the monoketal product.

Thus, another aspect of the present invention includes preparation of frovatriptan using the process described herein. The process for frovatriptan may require conversion of the monoketal product to a ketal of the formula:

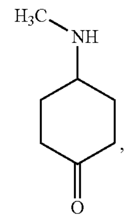

and cyclization of the ketal with 4-carboxamidophenylhydrazine. The detailed conditions for the processes of preparing Frovatriptan are known in the art, such as the methods described in U.S. Pat. No. 5,618,947 the entire content of which is herein incorporated by reference. For example, the desired ketal may be prepared by a reaction of the monoketal with methylamine. This reaction may be effected in a suitable solvent, for example a hydrocarbon such as benzene or toluene in the presence of titanium tetrachloride or suitable molecular sieves e.g. 4 Å molecular sieves, to give the corresponding iminoketal derivative which may then be converted to an alkylamino compound by catalytic hydrogenation using, for example, palladium on carbon. Alternatively the reaction may be effected in a solvent such as an alcohol, e.g. ethanol and the mixture hydrogenated directly, using, e.g., palladium on charcoal, to give the ketal compound.

The invention is illustrated by the following examples, which are not intended to limit the effective scope of the claims.

EXAMPLE 1

1,4 cyclohexane dione (20.0 grams) and neopentyl glycol (18.6 grams) were dissolved in dichloromethane (160 ml). Then sulfuric acid (3.2 grams) was added to the reaction solution at an ambient temperature and stirred till the reaction substantially completes, accompanied by cooling the reaction mixture to 10–20° C. The resulting reaction mixture was washed with saturated aqueous sodium bicarbonate solution (80 ml) and separated the organic layer from the resulting biphasic mixture. The solvent was distilled off from organic layer till substantial completion under reduced pressure. Hexane (200 ml) was added to the resulting residual mass and followed by cooling the reaction mass to a temperature of 0–5° C. to filter the by-products. Then the solvent from the filtrate was distilled off till the substantial completion under vacuum to yield the desired 1,4 cyclohexanedione mono-2,2-dimethyl trimethylene ketal.

(Weight: 22.9 grams)

EXAMPLE 2

1,4 cyclohexane dione (25.0 grams) and neopentyl glycol (23.5 grams) were dissolved in chloroform (200 ml). Then sulfuric acid (4.0 grams) was added to the reaction solution at an ambient temperature and stirred till the reaction substantially completes, accompanied by cooling the reaction mixture to 10–20° C. The resulting reaction mixture was washed with saturated aqueous sodium bicarbonate solution (100 ml) and separated the organic layer from the resulting biphasic mixture. The solvent was distilled off from organic layer till substantial completion under reduced pressure. Hexane (250 ml) was added to the resulting residual mass and followed by cooling the reaction mass to a temperature of 0–5° C. to filter the by-products. Then the solvent from the filtrate was distilled off till the substantial completion under vacuum to yield the desired 1,4 cyclohexanedione mono-2,2-dimethyl trimethylene ketal.

(Weight: 29.0 grams)

EXAMPLE 3

1,4 cyclohexane dione (25.0 grams) and neopentyl glycol (23.5 grams) were dissolved in dichloromethane (200 ml). Then sulfuric acid (4.0 grams) was added to the reaction solution at an ambient temperature and stirred till the reaction substantially completes, accompanied by cooling the reaction mixture to 10–20° C. The resulting reaction mixture was washed with saturated aqueous sodium bicarbonate solution (100 ml) and separated the organic layer from the resulting biphasic mixture. The solvent was distilled off from organic layer till substantial completion under reduced pressure. n-Heptane (250 ml) was added to the resulting residual mass and followed by cooling the reaction mass to a temperature of 0–5° C. to filter the by-products. Then the solvent from the filtrate was distilled off till the substantial completion under vacuum to yield the desired 1,4 cyclohexanedione mono-2,2-dimethyl trimethylene ketal.

(Weight: 30.0 grams).

Unless stated to the contrary, any use of the words such as "including," "containing," "comprising," "having" and the like, means "including without limitation" and shall not be construed to limit any general statement, the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

The invention claimed is:

1. A process for preparing a monoketal compound of the structure

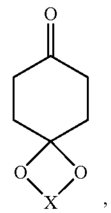

said process comprising reacting 1,4-cyclohexanedione of the structure

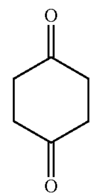

with a diol of the structure HO—X—OH in a halogenated organic solvent in the presence of an acid catalyst, wherein X is a substituted or unsubstituted ethylene or propylene.

2. The process of claim 1, wherein said diol is selected from the group consisting of ethylene glycol, propylene glycol, neopentyl glycol, and 1,3-propanediol.

3. The process of claim 2, wherein said diol is neopentyl glycol of the structure $HOCH_2C(CH_3)_2CH_2OH$.

4. The process of claim 3, further comprising a) converting said monoketal compound by reductive amination to an alkylamino ketal of the structure;

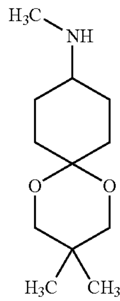

and b) reacting said alkylamino ketal with 4-carboxamidophenylhydrazine to form frovatriptan.

5. The process of claim 1, wherein said halogenated organic solvent is a $C_1$–$C_3$ haloalkane.

6. The process of claim 5, wherein said $C_1$–$C_3$ haloalkane is selected from the group consisting of chloroform, dichloromethane, dichloroethane, carbon tetrachloride and mixtures thereof.

7. The process of claim 6, wherein said $C_1$–$C_3$ haloalkane is dichloromethane.

8. The process of claim 6, wherein said $C_1$–$C_3$ haloalkane is chloroform.

9. The process of claim 3, wherein the molar ratio of 1,4-cyclohexanedione to neopentyl glycol ranges from about 1:1 to about 1:4, respectively.

10. The process of claim 9, wherein the molar ratio of 1,4-cyclohexanedione to neopentyl glycol ranges from about 1:1 to about 1:2, respectively.

11. The process of claim 10, wherein the molar ratio of 1,4-cyclohexanedione to neopentyl glycol is about 1:1, respectively.

12. The process of claim 1, wherein the weight/volume ratio of 1,4-cyclohexanedione to said halogenated organic solvent ranges from about 1:1 to about 1:20, respectively.

13. The process of claim 12, wherein the weight/volume ratio of 1,4-cyclohexanedione to said halogenated organic solvent is about 1:8, respectively.

14. The process of claim 1, wherein the reacting step includes dissolving 1,4-cyclohexanedione and said diol in said halogenated organic solvent and adding said acid catalyst to initiate the reaction.

15. The process of claim 1, wherein said acid catalyst is selected from the group consisting of hydrochloric acid, p-toluenesulfonic acid, sulfuric acid, fumaric acid, phthalic acid, oxalic acid and mixtures thereof.

16. The process of claim 15, wherein said acid catalyst is sulfuric acid.

17. The process of claim 1, wherein said reaction is performed at a temperature of from about 25° C. to about 50° C.

18. The process of claim 17, wherein said reaction is performed at a temperature of from about 25° C. to about 30° C.

19. The process of claim 1, further comprising removing said halogenated solvent to provide a crude residue; contacting said crude residue with an aliphatic or alicyclic hydrocarbon solvent; and removing solid impurities from the mixture.

20. The process of claim 19, wherein said aliphatic or alicyclic hydrocarbon solvent is selected from the group consisting of petroleum ether, hexane, n-hexane, cyclohexane, n-heptane, cycloheptane and mixtures thereof.

21. The process of claim 20, wherein said aliphatic or alicyclic hydrocarbon solvent is n-heptane.

22. The process of claim 19, wherein the removal of by-product(s) is achieved by filtration.

23. The process of claim 22, further comprising cooling the crude residue and the aliphatic or alicyclic hydrocarbon solvent to a temperature of from about 0° C. to about 25° C. before said filtration.

24. The process of claim 23, wherein said residue is cooled to a temperature of about 0° C.–5° C.

25. A process for preparing 1,4-cyclohexanedione mono-2,2-dimethyl trimethylene ketal, said process comprising:

a) reacting 1,4-cyclohexanedione and neopentyl glycol in dichloromethane or chloroform in the presence of sulfuric acid at about 25° C.–50° C.;

b) removing dichloromethane or chloroform to provide a crude residue;

c) combining an aliphatic or alicyclic hydrocarbon solvent with said crude residue to form a mixture;

d) cooling said mixture to a temperature of about 0° C.–5° C.; and e) filtering the cooled mixture to remove undissolved impurities.

26. A process for preparing frovatripan which comprises the steps of:

(a) reacting 1,4-cyclohexanedione of the structure

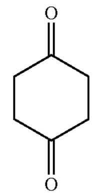

with a diol of the structure HO—X—OH in a halogenated organic solvent in the presence of an acid catalyst, wherein X is a substituted or unsubstituted ethylene or propylene, to form a monoketal compound of the structure:

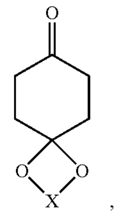

, b) converting the monoketal compound from step a) by reductive amination to an alkylamino ketal of the structure;

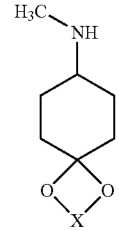

and c) reacting the alkylamino ketal from step b) with 4-carboxamidophenylhydrazine to form frovatripan.

27. The process of claim 26, wherein the diol is neopentyl glycol.

* * * * *